United States Patent [19]

Hachmeister

[11] 4,237,295

[45] Dec. 2, 1980

[54] PROCESS FOR THE PRODUCTION OF 17-HYDROXYSPARTEINE BY OXIDATION OF SPARTEINE WITH A PERMANGANATE

[75] Inventor: Bernd Hachmeister, Hannover, Fed Rep. of Germany

[73] Assignee: Kali-Chemie Pharma GmbH, Hannover, Fed. Rep. of Germany

[21] Appl. No.: 44,693

[22] Filed: Jun. 1, 1979

[30] Foreign Application Priority Data

Jun. 8, 1978 [DE] Fed. Rep. of Germany ....... 2825117

[51] Int. Cl.$^3$ .......................................... C07D 471/22
[52] U.S. Cl. ..................................................... 546/63
[58] Field of Search .......................................... 546/63

[56] References Cited

FOREIGN PATENT DOCUMENTS 2360475  6/1975  Fed. Rep. of Germany .

OTHER PUBLICATIONS

Rink et al., Chem. Abs. 51, 8114d (1956).
Skolik et al., Chem. Abs. 78, 72405u (1971).
Furuya et al., Chem. Abs. 78, 134443r (1973).
Willstatter et al., Chem. Ber. 38, 1772 (1905).

*Primary Examiner*—Mark L. Berch
*Attorney, Agent, or Firm*—Schwartz, Jeffery, Schwaab, Mack, Blumenthal & Koch

[57] ABSTRACT

Disclosed is the preparation of 17-hydroxysparteine by means of the oxidation of sparteine with permanganate in an aqueous acid solution. The oxidation is highly selective and produces the 17-hydroxysparteine in a high yield of more than 90%. The oxidizing agent may be readily separated from the reaction mixture after the reaction in the form of insoluble manganese ammonium phosphate.

10 Claims, No Drawings

PROCESS FOR THE PRODUCTION OF 17-HYDROXYSPARTEINE BY OXIDATION OF SPARTEINE WITH A PERMANGANATE

BACKGROUND OF THE INVENTION

The present invention pertains to a process for the production of 17-hydroxysparteine by means of the oxidation of sparteine in an aqueous acid solution.

The recent discovery of the advantageous pharmacological effects of different sparteine derivatives (DE-OS 23 60 475) prepared initially from 17-hydroxysparteine has generated a need for a technically and economically reasonable process for the production of 17-hydroxysparteine. In a known process (M. Rink, K. Grabowski, *Arch. Pharm.* 61 (1956), 695) sparteine is oxidized by means of chromium trioxide. The processing of the reaction mixture results in substantial amounts of aqueous solutions of chromium$^{III}$ and chromium$^{VI}$ salts, from which the very toxic chromic compounds may be separated only by means of expensive processes. Furthermore, the yield in 17-hydroxysparteine amounts to only 39%.

The oxidation of sparteine to 17-hydroxysparteine with the aid of the microorganism *Trametes gibbosa* is also known (K. Furuya, K. Aida, Y. Koiso, *Chem. Pharm. Bull.* 21 (1973), 231). This process operates with large volumes of liquid and is thus expensive, and it yields the desired 17-hydroxysparteine again in the relatively modest yield of 38%.

Oxidation with the ascorbic acid-iron$^{II}$-oxygen system (F. Jaminet, *J. Pharm. Belg.* 13 (1958), 577), which is highly time consuming, is merely of an academic character; after several days of reaction, it converts only part of the sparteine introduced.

SUMMARY OF THE INVENTION

It is thus an object of the present invention to provide an improved process for the preparation of 17-hydroxysparteine from sparteine.

It is another object of the invention to provide such a process wherein the disadvantages of the known processes are eliminated.

A particular object of the invention resides in providing an improved process which yields 17-hydroxysparteine in high proportions.

It is also an object to provide an improved process for the preparation of 17-hydroxysparteine which is simple in application and avoids reaction components which are toxic and difficult to separate.

In accomplishing the foregoing objects, there has been provided in accordance with the present invention a process for the production of 17-hydroxyspartine, comprising the step of oxidizing sparteine in an aqueous acid solution in the presence of a permanganate. Preferably, the oxidation step takes place in a solution of a mineral acid, most preferably sulfuric acid, at a PH within the range of from about 0 to 5, preferably from about 2 to 3.5, and at a temperature within the range of from about 0° to 100° C., preferably from about 0° to 20° C. Any watersoluble permanganate salt may be employed. Potassium permanganate is most preferred. In a preferred embodiment, the process further comprises the steps of precipitating Mn$^{II}$ formed during the oxidation step from the reaction mixture as a salt insoluble in water, preferably manganese ammonium phosphate, and separating the precipitated salt from the reaction mixture.

DETAILED DESCRIPTION OF PREFERRED EMBODIMENTS

The reaction according to the process of the invention is highly selective and produces 17-hydroxysparteine with a high yield of more than about 90%. Oxidation proceeds rapidly and is completed at maximum within approximately one hour. Processing is simpler than in chromic acid oxidation, because the Mn$^{II}$ salt formed is readily separated. Control of the reaction is simpler than that of chromic acid oxidation, since the latter, in contrast to the oxidation according to the invention, begins with a very strongly exothermic reaction.

Even though permanganate is known in certain other contexts as an oxidizing agent, and although the oxidation of sparteine to 17-hydroxysparteine is known per se, it could not have been expected that the action of permanganete on sparteine would proceed in the direction desired, because other, known oxidizing agents, such as mercury$^{II}$ acetate, potassium cyanoferrate$^{III}$ or hypobromite, lead to other products, for example, 5,6-didehydrosparteine, 5,6,11,12-tetrahydrosparteine, 17-oxosparteine or to dimer sparteines, respectively. It is also known from the older literature that sparteine is stable in relation to permanganate (R. Willstatter & W. Marx, *Chem. Ber.* 38 (1905), 1772). It was entirely unexpected, however, that oxidation by means of permanganate would proceed with such high selectivity and would produce 17-hydroxysparteine with the very high yield of more than 90%.

To initiate and maintain the acid reaction during the oxidation according to the present invention, in principle any acid, and especially any inorganic acid, for example, hydrochloric or sulfuric acid, may be used. Advantageously, a pH of from about 0 to 5 may be used, and optimally the process is operated in a sulfuric acid solution at a moderately acidic pH of approximately 2 to 3.5.

The temperature range wherein the oxidation is effected, is not critical; a range of approximately 0° to 20° C. is preferred according to the invention.

Any commercially available, water-soluble permanganate salt may be employed as the permanganate to effect the oxidation; potassium permanganate is preferred. In contrast to oxidation by chromic acid, where the 17-hydroxysparteine is precipitated as a chromate salt and is isolated as such, and whereby therefore, a corresponding excess of the oxidizing agent must be used, only a slight excess of the oxidizing agent is required in the oxidation with permanganate. Following completion of the oxidation, all of the manganese is present as Mn$^{II}$, which is readily precipitated as a salt insoluble in water and may then be separated, preferably as manganese ammonium phosphate. This may be accomplished merely by the addition of suitable amounts of water soluble ammonium and phosphate compounds after completion of the oxidation and by adjusting the reaction mixture to a neutral or weakly alkaline reaction. The 17-hydroxysparteine formed remains in the form of the salt in solution and may be extracted in a conventional manner, following separation of the manganese component.

In summary, 17-hydroxysparteine is produced according to the invention by adding solid permanganate or a permanganate solution to an aqueous solution of sparteine salt. The reaction is effected in a temperature range generally of from about 0° to 100° C., and preferably between about 0° and 20° C., in an acidic range of pH of from about 0 to 5, preferably with a pH of from about 2 to 3.5. The manganese$^{II}$ formed in the course of the reaction is precipitated in the form of cyrstalline manganese ammonium phosphate and is separated from the aqueous solution, wherein the basic product remains dissolved in the form of a salt. The 17-hydroxysparteine may be extracted in a strongly alkaline pH range from the aqueous solution with conventional organic extraction means.

The following non-limiting example will serve to more completely explain the invention:

EXAMPLE

A solution of 10.5 g potassium permanganate in 200 ml water is added to a solution cooled with ice of 42.4 g sparteine sulfate pentahydrate in 40 ml water. The rate of addition is controlled so that the internal temperature does not exceed 20° C. The simultaneous addition of sulfuric acid maintains the pH value between 2 and 3.5. After 40 minutes, the solution is briefly heated to 40° C., whereby any residual pyrolusite passes into solution. To the clear solution, 5.4 g ammonium chloride and 35.8 g di-sodium hydrogen phosphate ·12 H$_2$O, are added successively. Ammonium manganese phosphate is crystallized out by means of the addition of 15 ml 40% sodium hydroxide, after which it is suctioned off and washed with a small amount of water. The filtrate is made strongly alkaline with sodium hydroxide and is extracted with methylene chloride. Following drying of the organic phase and distillation of the extracting agent under vacuum, 23.8 g (=94.8% of theoretical) 17-hydroxysparteine remain in the form of oil.

This oil may be further processed without additional purification, for example, with Grignard compounds to 17-alkylsparteine according to DE-OS No. 23 60 475, the entire disclosure of which is hereby incorporated by reference.

If the organic phase is purified in the conventional manner with active carbon, then after the filtration of the active carbon and concentration of the solution, 22.6 g (=90% of theoretical) of a light yellow oil remain, which crystallizes after an extended period of standing. The crystals melt at 72°–75° C.

What is claimed is:

1. A process for the production of 17-hydroxysparteine, comprising the step of oxidizing sparteine in an aqueous acid solution in the presence of a water soluble permanganate.

2. A process according to claim 1, wherein said oxidation step takes place in a solution of a mineral acid.

3. A process according to claim 2, wherein said mineral acid comprises sulfuric acid.

4. A process according to claim 1, wherein the oxidation step is carried out at a pH within the range of from about 0 to 5.

5. A process according to claim 4, wherein the pH is between about 2 and 3.5.

6. A process according to claim 1, wherein the oxidation step is carried out at a temperature within the range of from about 0 to 100° C.

7. A process according to claim 6, wherein said temperature is between about 0° and 20° C.

8. A process according to claim 1, wherein said permanganate comprises potassium permanganate.

9. A process according to claim 1, further comprising the steps of precipitating Mn$^{II}$ formed during said oxidation step from the reaction mixture as a salt insoluble in water and separating the precipitated salt from the reaction mixture.

10. A process according to claim 9, wherein the Mn$^{II}$ is precipitated as manganese ammonium phosphate.

* * * * *